US007998484B2

(12) United States Patent
Griffiths et al.

(10) Patent No.: US 7,998,484 B2
(45) Date of Patent: Aug. 16, 2011

(54) NUCLEIC ACID AND AMINO ACID SEQUENCES OF INFECTIOUS SALMON ANAEMIA VIRUS AND THEIR USE AS VACCINES

(75) Inventors: Steven Griffiths, Monkton (CA); Rachael Jane Ritchie, Fredericton (CA); Joel Heppell, Chelsea (CA)

(73) Assignees: Novartis AG, Basel (CH); Ottawa Health Research Institute, Ottawa, Ontario (CA)

( * ) Notice: Subject to any disclaimer, the term of this patent is extended or adjusted under 35 U.S.C. 154(b) by 0 days.

(21) Appl. No.: 12/624,918

(22) Filed: Nov. 24, 2009

(65) Prior Publication Data

US 2010/0136038 A1 Jun. 3, 2010

Related U.S. Application Data

(60) Continuation of application No. 11/525,695, filed on Sep. 22, 2006, now abandoned, which is a continuation of application No. 10/734,782, filed on Apr. 2, 2004, now Pat. No. 7,128,917, which is a division of application No. 10/049,086, filed as application No. PCT/GB00/02976 on Aug. 7, 2000, now Pat. No. 6,919,083.

(30) Foreign Application Priority Data

Aug. 7, 1999 (GB) .................................. 9918588.6
Mar. 11, 2000 (GB) .................................. 0005848.7
Mar. 21, 2000 (GB) .................................. 0006674.6

(51) Int. Cl.
*A61K 39/12* (2006.01)

(52) U.S. Cl. ................ 424/186.1; 424/204.1; 536/23.72

(58) Field of Classification Search ........................ None
See application file for complete search history.

(56) References Cited

U.S. PATENT DOCUMENTS 6,471,964 B1 10/2002 Biering et al.

FOREIGN PATENT DOCUMENTS

| | | | |
|---|---|---|---|
| EP | 1180041 | B1 | 3/2006 |
| EP | 1637614 | A2 | 3/2006 |
| EP | 1200132 | B1 | 7/2007 |
| WO | WO/00/72878 | | 12/2000 |
| WO | WO/ 01/ 49712 | | 1/2001 |
| WO | WO/01/66569 | | 9/2001 |
| WO | WO/02/26784 | | 4/2002 |

OTHER PUBLICATIONS

Rocco C. Cipriano, Infectious Salmon Anemia Virus, US Geological Survey, Fish Disease Leaflet #85, 2003, pp. 1-11, available from www.lsc.usgs.gov/fhb/leaflets/FHB85.pdf.*

Anderson, D.P., "Adjuvants and Immunostimulats for Enhancing Vaccine Potency in Fish," Dev. Biol. Stand. 90:257-265 (1997).

Blake, S. et al., "Genomic Relationships of the North American Isolate of Infectious Salmon Anemia Virus (ISAV) to the Norwegian Strain of ISAV," Dis. Aquat. Org. 35(2):139-144, XP000984527 (1999).

Davis, H. et al., "DNA Vaccines for Viral Diseases," Microbes and Infection, 7-21 (1999).

Falk, K. et al., "Demonstration of a Protective Immune Response in Infectious Salmon Anaemia (ISA)-infected Atlantic Salmon *Salmo salar,*" Dis. of Aquat. Org., 21:1-5 (1995).

Falk, K., et al., "Characterization and Applications of a Monoclonal Antibody Against Infectious Salmon Anaemia Virus," Dis. of Aquat. Org., 34:77-85 (1998).

Falk, K., et al., "Characterization of Infectious Salmon Anemia Virus an Orthomyzo-Like Virus Isolated from Atlantic Salmon (*Salmo salar* L.)," Journal of virology, 71(12):9016-9023 (1997).

Griffiths, et al., "Charactrization of ISAV Proteins from Cell Culture," Dis. of Aquat. Org., 45:19-24 (2001).

Horne, M.T., "Technical Aspects of the Administration of Vaccines," Dev. Biol. Stand., 90:79-89 (1997).

Kanellos, T., et al., "The Safety and Longevity of DNA Vaccines for Fish," Blackwell Science Ltd Immunology, 96:306-313 (1999).

Kibenge, et al., "Antigenic Variation Among Isolates of Infectious Salmon Anaemia Virus Correlates with Genetic Variation of the Viral Haemagglutinin Gene," Journal of General Virology, 82:2869-2879 (2001).

Krossy, B., et al., "Cloning and Identification of the Infectious Salmon Anaemia Virus Haemagglutinin," Journal of General Virology, 82:1757-1765 (2001).

Krossy, B., et al., "The Putative Polymerase Sequence of Infectious Salmon Anemia Virus Suggests a New Genus within the Orthomyxovirdae," Journal of Virology, 73(3):2136-2142, XP000986368 (1999).

Leong, J.C., et al., "Fish Vaccine Antigens Produced or Delivered by Recombinant DNA Technologies," Dev. Biol. Stand. 90:267-277 (1997).

Lorenzen, N., et al., "Immunization with viral antigens: Viral Haemorrhagic Septicaemia," Dev. Biol. Stand., 90:201-209 (1997).

Lovely, J.E., et al., "First Identification of Infectious Salmon Virus Anaemia Virus in North America with Haemorrhagic Kidney Syndrome," Dis. of Aquat. Org., 35(2): 145-148, XP000984528 (1999).

Mjaaland, et al., "Genomic Characterization of the Virus Causing Infectious Salmon Anemia in Atlantic Salmon (*Salmo salar* L.): an Orthomyxo-Like Virus in Teleost," Journal of Virology, 71(10):7681-7686 (1997).

Rimstad, et al., "Characterization of the Infectious Salmon Anemia Virus Genomic Segment that Enclosed the Putative Haemagglutinin," Journal of Virology, 75(11):5352-5356 (2001).

Ritchie, et al., Virus Genes, 22(3):289-297 (2001).

Winton, J.R., "Immunization with Viral Antigens: Infectious Haematopoietic Necrosis," Dev. Biol. Stand., 90:211-220 (1997).

* cited by examiner

*Primary Examiner* — Stacy B Chen

(57) ABSTRACT

The present invention provides the use of nucleic acid sequences and/or amino acid sequences in the preparation of a vaccine for the protection of fish against infectious salmon anemia virus. Specifically, such vaccines contain at least one nucleic acid sequence which is derived from ISAV or synthetically prepared analogues thereof, or substantially homologous sequences. These nucleic acid sequences are transcripted and translated into peptide sequences which are incorporated into a vaccination strategy to induce and immune response to the surface antigens of ISAV and therefore ISAV itself. Therefore both the use of a vaccine against ISAV, and the incorporation of peptide sequences is herein described.

9 Claims, 10 Drawing Sheets

Figure 1: ISA2cd Nucleotide Sequence

```
caagatggat aacctccgtg aatgcataaa ccgcaaaaga agactacttg ccttaccaga     60
tgttcctgaa acttcggatg cctttctaag tgatttgaga catctataca tgtgtgttgc    120
tttctgtgat caacacaaaa ccactggaga cgaatcaaga ttcaccaacc tggaattact    180
tgaccaagat gaagcactag gtgcccaaag agctttgaa gccaaacatg gaataaagg      240
aggttcttta ggagacgttc ttgaccatga actgaaaaag gtcattgaat ttacttttac    300
ttctggaagt ttgtatattg ccgaacaaag aaaaagaaag actcaagcag actcaataat    360
tgtgtgcgtt tcagaaggac ttaacgactt cagcgtatca cacggagtgc tagacatggg    420
acttgtggaa acaggggtga atgcagtaag agatttctgc acacaaaacg gaataccaat    480
gaagataaat caggtaggat ccacgagaac accaacaccg atcagcacat gcaaaatctc    540
tgaacaaata acacgacaga taaacagtac aattactgaa aggaaaatgg aaacagtact    600
ggcagcaatc gcaattaaac cagaactcaa actaactcag aaaggatgca gaccttgtaa    660
agaactagaa gatgaaaata ttctgtggat ggaccctcaa ttctgtgaaa ttgatgaaag    720
ttttccttac agaggagggc catacgggaa cttcctgcaa gaattgctgc ttacaaccaa    780
cgacgtagag accaacggga aagacagaga agaagtagta aagaagatac tggataacaa    840
ggcgttcacc gttgaaagtg gtgaatgcat aataacactt ccagacaaaa tgacttgttt    900
cggagaacag gagaagaaga gaccagcaac aatagacgaa gtgagaaccg caggagaaag    960
gtttgaacag agtgttaaac cgaaaaccca aagatatgga aggttatcag acaaatggat   1020
ggagcttgaa aagtttatct ttactgcaag caaaacagaa gtggatactt tcctttctgt   1080
agggaccgaa agacttgagt cggttggagt gtgtgtcgga gctttacaca gagcgaccac   1140
aaccaggata attagaccta tgattcaagg agggaaatgt tgggggatga tgttcaaaac   1200
aaagtccaaa atgggagaca cgaggaagga aggatactgt cacgcaatca ttttcggaaa   1260
aggggaagat aaatcaggac aaaacaagat gacaatgatg ggaaaacag tacattggca    1320
tctaagagta gttaagtcta aaggagactg gatggcgcaa caactctgtg caaacaaaag   1380
cagaatatgg gaacatgacc ctgagctagt aacagaagga gtgacagttc taatgacgcc   1440
tttttctcag aaaattgcca ccattagtag atggagggca atgaggttag acagcatgtt   1500
tcatgtttct agtgcctggc atcattcacc tgcgtgtgaa gctgcatcgg caatgctgag   1560
aaagtttgtg gagatagtac atgccatcaa ccagaaaaga gattggggtg ttgtggggag   1620
tatggaggac atggtgaagg aagtggagga aatagggag cacttgcaga cggcatgtga    1680
ttttagagtt tacaacatgt gcaaagcctt gattcagaaa attgcagtca gtacccaatg   1740
agtggttatt tacttgtaaa ttgttgtgtg tttgacgata tgtatttgtc gacgcggccg   1800
cggtcgacgc ggccgcgaat t                                              1821
```

Figure 2: ISA2cd Amino Acid Sequence

| | 1 | 11 | 21 | 31 | 41 | 51 | |
|---|---|---|---|---|---|---|---|
| 1 | MDNLRECINR | KRRLLALPDV | PETSDAFLSD | LRHLYMCVAF | CDQHKTTGDE | SRFTNLELLD | 60 |
| 61 | QDEALGAQRA | FEAKHGIKGG | SLGDVLDHEL | KKVIEFTFTS | GSLYIAEQRK | RKTQADSIIV | 120 |
| 121 | CVSEGLNDFS | VSHGVLDMGL | VETGVNAVRD | FCTQNGIPMK | INQVGSTRTP | TPISTCKISE | 180 |
| 181 | QITRQINSTI | TERKMETVLA | AIAIKPELKL | TQKGCRPCKE | LEDENILWMD | PQFCEIDESF | 240 |
| 241 | PYRGGPYGNF | LQELLLTTND | VETNGKDREE | VVKKILDNKA | FTVESGECII | TLPDKMTCFG | 300 |
| 301 | EQEKKRPATI | DEVRTAGERF | EQSVKPKTQR | YGRLSDKWME | LEKFIFTASK | TEVDTFLSVG | 360 |
| 361 | TERLESVGVC | VGALHRATTT | RIIRPMIQGG | KCWGMMFKTK | SKMGDTRKEG | YCHAIIFGKG | 420 |
| 421 | EDKSGQNKMT | MMGKTVHWHL | RVVKSKGDWM | AQQLCANKSR | IWEHDPELVT | EGVTVLMTPF | 480 |
| 481 | SQKIATISRW | RAMRLDSMFH | VSSAWHHSPA | CEAASAMLRK | FVEIVHAINQ | KRDWGVVGSM | 540 |
| 541 | EDMVKEVEEI | GEHLQTACDF | RVYNMCKALI | QKIAVSTQ | | | |

Molecular weight: 65336.10

Theoretical pI: 6.94

Figure 3: ISA1mta Nucleotide Sequence

```
gcaaagatyg ctcaaatccc aaaaataata cagaaaacgt ataagagatg gccgataaag   60
gtatgactta ttcttttgat gtcagagaca acaccttggt tgtaagaaga tctaccgcta  120
ctaaaagtgg cattaagatc tcctacagag aggatcgagg aacatcactt ctccaaaagg  180
cattcgccgg gacagaagat gaattctggg tggagttaga tcaagatgtc tacgttgaca  240
aaaagattag aaaattcctg gaagaagaga aaatgaagga catgagcaca agagtgtctg  300
gagcagtggc agcagcaatt gaaagatcag ttgaatttga caatttctca aaagaagcag  360
cagctaacat tgaaatggct ggtgtagatg atgaagaagc tggaggaagt ggtctggtag  420
acaacagaag gaagaacaaa ggggtctcaa acatggccta caatctgtct ctattcatag  480
ggatggtgtt tcctgctctc actactttct tcagtgctat cctatcagaa ggtgaaatga  540
gcatctggca aaatggacaa gcaatcatca gaattctggc actggcagat gaagacggaa  600
agagacaaac aagaacagga ggacagaggg tggacatggc tgatgtaacc aagctgaacg  660
tagtcacggc taacgggaaa gtcaagcaag ttgaagtaaa cttgaacgat ctcaaagcag  720
cattcaggca gagtagacct aaaagatcgg actacagaaa agggcaaggt tccaaggcta  780
cagaatcaag catctccaac caatgtatgg cactgattat gaaatctgtg ctgtcagcag  840
accaactttt tgctccggga gtgaagatga tgaggacgaa cggtttcaat gcgtcgtaca  900
caacactggc agaaggggca aacattccga gcaagtacct aagacacatg aggaactgcg  960
gaggagtagc tctggacctg atgggaatga agaggatcaa aaactcacct gaaggagcca 1020
agtctaagat cttttccatc atccagaaga aagtaagagg aagatgtcgc acagaggagc 1080
aacgcctcct gactagcgca ctgaaaatca gcgacggtga aaacaagttc cagagaatca 1140
tggacactct atgtacaagc ttcctgattg accctccaag aactaccaaa tgcttcattc 1200
cacctatttc cagtctcatg atgtacatcc aagaaggcaa ctctgtactg gcaatggatt 1260
tcatgaaaaa cggagaggac gcctgcaaga tctgcagaga agccaaactg aaagtggggg 1320
taaacagtac gttcacaatg tcagtagcta gaacatgcgt tgcagtgtca atggttgcaa 1380
cagctttttg ttctgcagat atcatcgaga atgcagtgcc tggttccgaa aggtacagat 1440
ccaacatcaa ggctaacaca accaaaccaa aaaaggactc cacttacaca attcaaggac 1500
ttagattgtc taacgtgagg tatgaagcaa gacctgaaac atcacaaagc aacacagaca 1560
gaagttggca agtgaacgtg actgacagct tcggaggact tgctgtgttc aaccaagggg 1620
caattagaga aatgctagga gacggaacat cagagacaac tagtgtgaac gtcagagccc 1680
tggtgaagag aattctgaaa tcagcttcag agaggagtgc aagagctgta aagacattta 1740
tggtgggaga acaagggaaa tcagctattg ttatctctgg tgtgggactg ttctctattg 1800
actttgaagg ggtagaggaa gcggaaagga taactgacat gacacctgaa attgagtttg 1860
acgaggacga cgaggaagag gaagacattg acatttagag tgacaattat gtaactttct 1920
aattacccta tattgtttga atatataatg aaactattgt gtgttaaagg ttgtgggttt 1980
gattattaaa tttaaattga aacggtattg acgatatt                         2018
```

Figure 4: ISA1mta Amino Acid Sequence

```
    1          11         21         31         41         51
    |          |          |          |          |          |
  1 MADKGMTYSF DVRDNTLVVR RSTATKSGIK ISYREDRGTS LLQKAFAGTE DEFWVELDQD    60
 61 VYVDKKIRKF LEEEKMKDMS TRVSGAVAAA IERSVEFDNF SKEAAANIEM AGVDDEEAGG   120
121 SGLVDNRRKN KGVSNMAYNL SLFIGMVFPA LTTFFSAILS EGEMSIWQNG QAIIRILALA   180
181 DEDGKRQTRT GGQRVDMADV TKLNVVTANG KVKQVEVNLN DLKAAFRQSR PKRSDYRKGQ   240
241 GSKATESSIS NQCMALIMKS VLSADQLFAP GVKMMRTNGF NASYTTLAEG ANIPSKYLRH   300
301 MRNCGGVALD LMGMKRIKNS PEGAKSKIFS IIQKKVRGRC RTEEQRLLTS ALKISDGENK   360
361 FQRIMDTLCT SFLIDPPRTT KCFIPPISSL MMYIQEGNSV LAMDFMKNGE DACKICREAK   420
421 LKVGVNSTFT MSVARTCVAV SMVATAFCSA DIIENAVPGS ERYRSNIKAN TTKPKKDSTY   480
481 TIQGLRLSNV RYEARPETSQ SNTDRSWQVN VTDSFGGLAV FNQGAIREML GDGTSETTSV   540
541 NVRALVKRIL KSASERSARA VKTFMVGEQG KSAIVISGVG LFSIDFEGVE EAERITDMTP   600
601 EIEFDEDDEE EEDIDI
```

Molecular weight: 68050.47

Theoretical pI: 8.20

Figure 5: ISA3mx Nucleotide Sequence

```
atgtctggat ttaacctcga ggtaatggtg ccggaacaag gaggaaaagt ggtcttcagc      60
cttactgaaa cggggtcatg tgtctcgttt tacggagatg atgaaccagg tgaagggtcc     120
tgcgaacttg cctctgaaaa catggatttt ccaagttgtc ctctggggaa tggagatgac     180
ttctgtctgt cgctggcgct aagcacaatg agatggtctg ggatgaccaa gagaaacaac     240
ttcatggaca gattcattgg aagttttgtt cactgtacac cagtgatgat ctggtcgtat     300
ggaaatttgt ccaagaaaag ccatcacaaa atggtttgcc acacttgccc agacgagtac     360
aagttcagtg acaaggacga gatgcaggga tactatgagg gatgtctaga ggcttctact     420
gacattttcc ttgatgaact tgctactgtt gttacaggtg gcttctttcc tgtcggactc     480
aaaggttcct ggggaggatg gtacctcaag tacgtcaggt atgctggacc tcttgcggga     540
tcaagtggat tcattgtcaa tcaacgattc tacgacagag cccaaaacaa gactggatcc     600
agggttgtat ccatggttga aatggacgga gacggcttat cgttcatcta cgagaagcct     660
agcgtctacc atagtgacgg gtgcactggg tcagcagcga ggttctggaa acgggatcac     720
aatgagagag ctggagttga gcttagggct ggacttcact tcagaatgtg attggttgaa     780
aacttgttat gtaaacaaga attttgtgtt tttgtcagaa aaagaaattg ctgtaaacat     840
ggaagttgaa aaattcattt gtaatgagaa ctaaagatgt ctttgtgttc aaattttaac     900
taatgacaat atatgaaata tgtcgtacat ggtgttgatg ataattttta aaacgaaaag     960
gagaattttt actaaaataa aaaaaaaata aaaaaaaaaa aaaagaaaaa aaaaaaaaaa    1020
aaaaaaagtc gacatcgata cgcgtggtca                                     1050
```

Figure 6a: Predicted Amino Acid Sequence of unspliced (M1) product of ISA3mx

MSGFNLEVMVPEQGGKVVFSLTETGSCVSFYGDDEPGEGSCELASENMDFPSCPLGNGDD 60

FCLSLALSTMRWSGMTKRNNFMDRFIGSFVHCTPVMIWSYGNLSKKSHHKMVCHTCPDEY 120

KFSDKDEMQGYYEGCLEASTDIFLDELATVVTGGFFPVGLKGSWGGWYLKYVRYAGLAG 180

SSGFIVNQRFYDRAQNKTGSRVVSMVEMDGDGLSFIYEKPSVYHSDGCTGSAARFWKRDH 240

NERAGVELRAGLHFRM 256

Molecular weight: 28,498

Theoetical pI: 5.38

Figure 6b: Predicted Amino Acid Sequence of spliced (M2) product of ISA3mx

MSGFNLEVMVPEQGGKVVFSLTETGSCVSFYGDDEPGGFFPVGLKGSWGGSYLKYVRYAG 60

PLAGSSGFIVNQRFYDRAQNKTGSRVVSMVEMDGDGLSFIYEKPSVYHSDGCTGSAARFW 120

KRDHNERAGVELRAGLHFRM 140

Molecular weight: 15,357

Theoetical pI: 6.82

Figure 6c: Predicted Amino Acid sequence of spliced (M3) product of ISA3mx

MNLLLLLQVASFLSDSKVPGEDGTSSTSGMLDLLRDQVDSLSINDSTTEPKTRLDPGLYP 60

WLKWTETAYRSSTRSLASTIVMGALGQQRGSGNGITMRELELSLGLDFTSECDWLKTCYV 120

NKNFVFLSEKEIAVNMEVEKFICNEN 147

Molecular weight: 14,888

Theoretical pI: 4.65

Figure 7: ISA4ha Nucleotide Sequence

```
cagtcgtcta tgtcttagaa accatcctga caccacctgg ataggtgact cccgaagcga    60
tcaatcaagg gtgaaccaac agtctcttga tctggttaca aacttcaagg gaattctaca   120
agccaagaac gggaatggtc tcatgaagca gatgagcgga aggttcccaa gtgattggta   180
ccaacctact acaaagtata ggattctata cattggtaca aacgactgca ctgagggccc   240
taacgacgtg atcataccga cgtcaatgac actagacaat gtggcaaggg acctgtacct   300
gggagcatgt cgaggagatg taagagtgac accaaccttc gtgggagcag ctgagcttgg   360
actgattggg agaacagatg ccttaacagg attttctgta aaggtgctga ctttcaacaa   420
ccctactatt gtagtagttg gactaaatgg aatgtcagga atctacaagg tctgcattgc   480
tgcctcttct ggaaacgtag gcggagtcaa cttggtgaac ggatgcggat acttcagcgc   540
tcctctgaga ttcgacaact tcaaaggaca gatctacgtg tcagacacct ttgaagtcag   600
aggaacaaag aacaaatgtg tcatacttag atcttctagc aatgctcctt tgtgtacaca   660
tatcaaaaga aacattgagt tggatgagta cgttgacaca ccaaacactg ggggcgtata   720
tccttctgat gggtttgatt ctcttcacgg ctctgcttcg attagaactt ttttaacaga   780
ggcactgaca tgtccaggtg tagattggga cagaattgat gcagcttcat gcgagtatga   840
cagttgtcct aaacttgtga aagaatttga ccaaacaggg ctcggaaaca cagatactca   900
aataatgaga gagctagaag cacaaaagga gatgattggt aaacttggca gaaacattac   960
agacgtaaac aacagagtag atgctattcc accacagctt agcaacatct tcatctctat  1020
gggagtggca ggt                                                     1033
```

Figure 8: ISA4ha Amino Acid Sequence

```
         1          11         21         31         41         51
         |          |          |          |          |          |
    1 SRLCLRNHPD TTWIGDSRSD QSRVNQQSLD LVTNFKGILQ AKNGNGLMKQ MSGRFPSDWY     60
   61 QPTTKYRILY IGTNDCTEGP NDVIIPTSMT LDNVARDLYL GACRGDVRVT PTFVGAAELG    120
  121 LIGRTDALTG FSVKVLTFNN PTIVVVGLNG MSGIYKVCIA ASSGNVGGVN LVNGCGYFSA    180
  181 PLRFDNFKGQ IYVSDTFEVR GTKNKCVILR SSSNAPLCTH IKRNIELDEY VDTPNTGGVY    240
  241 PSDGFDSLHG SASIRTFLTE ALTCPGVDWD RIDAASCEYD SCPKLVKEFD QTGLGNTDTQ    300
  301 IMRELEAQKE MIGKLGRNIT DVNNRVDAIP PQLSNIFISM GVAG
```

Molecular Weight: 37,437

Theoretical pI: 5.38

NUCLEIC ACID AND AMINO ACID SEQUENCES OF INFECTIOUS SALMON ANAEMIA VIRUS AND THEIR USE AS VACCINES

The present application is a Continuation of U.S. application Ser. No. 11/525,695 filed Sep. 22, 2006, now abandoned, which is a Continuation of Ser. No. 10/734,782 filed Apr. 2, 2004, now U.S. Pat. No. 7,128,917, which is a Division of Ser. No. 10/049,086 filed May 30, 2002 filed as National Phase Entry under §371 of International Application No. PCT/GB00/02976 filed Aug. 7, 2000, now U.S. Pat. No. 6,919,083, which claims the benefit of priority to G.B. Application No. 9918588.6 filed Aug. 7, 1999, G.B. Application No. 0005848.7 filed Mar. 11, 2000, and G.B. Application No. 0006674.6 filed Mar. 21, 2000, the entire contents of each of which are herein incorporated by reference in their entirety.

The present invention relates to a fish vaccine. More specifically the invention relates to a vaccine to protect salmon against infectious salmon anaemia virus.

Infectious salmon anaemia virus (ISAV) causes mortality of farmed Atlantic salmon. Typically aquaculture revenue is reduced by over 30%. Accordingly, there is a need for an effective vaccine against ISAV.

It is an object of the present invention to provide a vaccine to protect against ISAV.

According to the present invention there is provided a composition containing at least one nucleic acid sequence and/or at least one amino acid sequence, or a synthetically prepared analogue thereof or a substantially homologous sequence, wherein the composition is derived from or based upon infectious salmon anaemia virus and wherein at least one of said nucleotide and/or amino acid sequences does not cause salmon anaemia and is capable of being used as or to prepare a vaccine to ISAV.

A substantially homologous nucleic acid sequence is a sequence which can be transcribed and/or translated to provide an amino acid sequence which is substantially homologous to at least a part of an antigen of ISAV.

Preferably the substantially homologous amino acid is at least 70% homologous with a part of an antigen of ISAV which is capable of inducing an immune response.

More preferably the substantially homologous amino acid sequence is at least 80% homologous with a part of an antigen of ISAV and can induce an immune response.

Most preferably the substantially homologous amino acid sequence is at least 90% homologous with a part of an antigen of ISAV and can induce an immune response.

Suitably the amino acid sequence is chosen from the group comprising Sequences ID numbers 2, 4, 6, 7, 8 or 10 as herein described.

Alternatively the amino acid sequence may comprise at least one fragment of Sequence ID numbers 2, 4, 6, 7, 8 or 10.

Alternatively said amino acid sequence may be truncated from an amino acid sequence of Sequences ID numbers 2, 4, 6, 7, 8 or 10 as herein described, which can induce an immune response.

Preferably the substantially homologous nucleotide sequence is at least 60% homologous with a part of a nucleic acid sequence of an antigen of ISAV and the translation product thereof is capable of inducing an immune response.

Preferably the substantially homologous nucleotide sequence encodes at least 70% homologous with a part of a nucleic acid sequence of an antigen of ISAV, the translation product of which is capable of inducing an immune response.

More preferably the substantially homologous nucleotide sequence encodes at least 80% homologous with a part of a nucleic acid sequence of an antigen of ISAV, the translation product of which is capable of inducing an immune response.

Most preferably the substantially homologous nucleotide sequence is at least 90% homologous to a part of a nucleic acid sequence of an antigen of ISAV, the translation product of which is capable of inducing an immune response.

Suitably the nucleotide sequences are chosen from the group comprising Sequence ID numbers 1, 3, 5 or 9 as herein described.

Alternatively, the invention provides for fragments of the sequences described in Sequence ID numbers 1, 3, 5 and 9 as herein described and wherein translation products of said fragments result in the induction of an immune response.

Additionally, the sequences may comprise a truncated form of the sequences given as 1, 3, 5 and 9.

The nucleotide sequence may be incorporated in a plasmid.

The nucleotide sequence may be incorporated in a suitable expression vector.

A further aspect of the present invention provides for the use of a sequence chosen from the group consisting of Sequence ID numbers 1 to 10, as described in the present invention in the preparation of a vaccine and/or therapeutic medicament for the protection of fish from infection with Infectious Salmon Anaemia virus.

Typical nucleic acid sequences are ISA2cd (previously referred to as p1.38), ISA1mta (previously referred to as p8.17), ISA3mx (previously referred to as p6.28) and ISA4ha.

Preferably the peptide sequences are transcribed and translated from either one, two or all of the nucleic acid sequences; ISA2cd, ISA1mta, ISA3mx or ISA4ha and are incorporated into a vaccination strategy aimed at inducing an immune response to a surface antigen of ISAV and thus infectious salmon anaemia virus itself.

The invention provides the use of nucleic acid sequences or peptide sequences as defined herein in the preparation of a vaccine for the protection of fish against ISAV.

The invention further provides a vaccine to protect fish against ISAV wherein the vaccine includes nucleic acid or peptide sequences as defined herein.

CHARACTERISATION OF THE NOVEL SEQUENCES OF THE INVENTION

The accompanying figures describe the invention in more detail, wherein;

FIG. 1 is the nucleotide sequence of ISA2cd,

FIG. 2 is the amino acid sequence which is obtained from translation of the ISA2cd nucleic acid sequence listed in FIG. 1, FIG. 3 is the nucleotide sequence of ISA1mta, FIG. 4 is the amino acid sequence which is obtained following transcription of the nucleic acid sequence listed in FIG. 3, FIG. 5 is the exact nucleotide sequence of ISA3mx, FIG. 6*a* is the amino acid sequence (M1) which is translated from the unspliced nucleic acid sequence of ISA3mx shown in FIG. 5, FIG. 6*b* is the amino acid sequence (M2) which is translated from the spliced nucleic acid sequence of ISA3mx shown in FIG. 5, and FIG. 6*c* is the amino acid sequence (M3) which is translated from the unspliced nucleic acid sequence of ISA3mx as shown in FIG. 5.

FIG. 7 is the nucleotide sequence of ISA4ha (SEQ ID NO:9).

FIG. 8 is the amino acid sequence of ISA4ha (SEQ ID NO: 10).

In addition, information detailing the specific molecular weight (MW) and theoretical isoelectric focusing points (pI) is given at the foot of the respective amino acid sequence listings.

The nucleotide and amino acid sequences shown in the figures are further represented in the accompanying Patent-In generated sequence listings wherein;

Sequence ID number 1 is the nucleotide sequence of ISA2cd, as shown on FIG. 1, Sequence ID Number 2 is the amino acid sequence of the ISA2cd, as shown in FIG. 2, Sequence ID number 3 is the nucleotide sequence of ISA1mta, as shown on FIG. 3, Sequence ID number 4 is the amino acid sequence of ISA1mta, as shown on FIG. 4, Sequence ID number 5 is the nucleotide sequence of ISA3mx, as shown on FIG. 5, Sequence ID number 6 is the predicted amino acid sequence of unspliced product of ISA3mx, as shown in FIG. 6*a,*

Sequence ID number 7 is the predicted amino acid sequence of spliced ISA3mx, as shown in FIG. 6*b,*

Sequence ID number 8 is the predicted amino acid sequence of spliced ISA3mx, as shown in FIG. 6*c,*

Sequence ID number 9 is the nucleotide sequence of ISA4ha, as previously shown in FIG. 7, and Sequence ID number 10 is the amino acid sequence of ISA4ha, as previously shown in FIG. 8.

The genetic sequences shown for ISA1mta and ISA2cd and the unspliced and spliced genetic sequences for ISA3mx have been derived from cloned cDNA wherein the cDNA clones were derived from infectious salmon anaemia virus (ISAV) genomic material. The cloned material was sequenced from the 5' end and the 3' end insertion sites using overlapping amplicons to produce a contig.

Veracity of the contig was confirmed by Reverse Transcriptase Polymerase Chain Reaction amplification (RT-PCR) of appropriate sized amplicons from ISAV infected salmon tissue and tissue cultures. Such amplicons were however obtained from uninfected control material, indicating that the genetic material was of ISAV origin.

The open reading frames (ORFs) were completed by rapid amplification of cDNA ends (RACE) from the incomplete sequence from virus-infected tissue culture. Corrections were made for the in vivo transcribed mRNA that were not apparent from the originally cloned cDNAs.

The ORF from ISA2cd does not have any significant homology at the nucleotide or amino acid sequence with previous submissions to databases accessible by BLAST. However, proteins with similar molecular weights (Mw) and isoelectric points (pI) include 14 viral proteins in the Swiss-Prot database such as Hemagglutinin-Neuraminidase.

The ORF from ISA1mta is also without any significant homology to previously characterised proteins submitted to the BLAST searchable databases. However it is of interest that it has molecular weight and isoelectric point characteristics (68-69 kDa and pI 8.2) that are nearly identical to one of the most predominant viral proteins identified by two dimensional electrophoresis. The protein appears to be integrally associated with the membranes of the ISAV infected tissue cultures. If the ORF yields such a protein it would be considered valuable in any vaccination strategy to reduce the level of ISAV infection in any salmonoid species.

Further, in the sequences shown for ISA3mx, the unspliced ORF (the basis for predicted amino acid sequence M1) does not have any significant homology at the nucleotide or amino acid sequence level with the previous submission to databases accessible by BLAST. However, proteins with similar molecular weights and isoelectric focusing points include several viral coat and envelope proteins listed in the Swiss-Prot database. Both the predicted M1 and M2 proteins (obtained from ORF's following splicing of the nucleotide sequence) are predicted to be membrane associated proteins and if the ORFs encoded by ISA3mx yield such proteins it would be considered valuable in any vaccination strategy to reduce the level of ISAV infection in any salomonid species.

The predicted protein translation of M3 (shown in FIG. 6*c* and accompanying sequence listing) shows homology to a paromyxovirus fusion protein associated with the cell membrane and thought to be involved in cell adhesion. In view of this exhibited homology, M3 is potentially valuable in any vaccination strategy aimed at reducing the level of ISAV infection in any salmonid species.

The further sequence relating to ISA4ha nucleotide sequence was obtained by means of the following procedure. The ISA4ha protein was detected by polyclonal antibodies following hybridisation. The protein is found to occur in two alternative forms.

These two alternative forms are of different sizes, and can be seen where the proteins are cultured on different cell lines, for example she and chse.

As these two alternate forms were both detectable by antibody and varied in size depending on how it was grown, the protein is potentially a good candidate for virulence.

The protein was isolated and sequenced, resulting in a 24 amino acid fragment being produced. When this sequence was submitted, to BLAST searchable databases, it showed similarities to sequences of British and Norwegian strains of ISAV.

Subsequently, primers were designed based on the amino acid sequence obtained, along with reference to the sequences known for the similar British and Norwegian strains.

The primers were then subsequently used in polymerase chain reaction to amplify the relevant DNA fragment, which was subsequently sequenced and translated into amino acid coding.

The open reading frame listings obtained in the present invention, have particular commercial value for the following reasons:

1. There is sufficient reason to believe that the nucleotide corresponding amino acid sequences are of ISAV origin. Therefore, their incorporation into nucleic acid vaccines may have an impact on the reduction of mortality of farmed Atlantic salmon caused by ISAV which as previously stated, can typically reduce aquaculture revenues by over 30%.
2. Characterisation of the gene product will lead to the identification of key elements in the pathogenesis of infection and to the design of more accurate diagnostic tests which will also aid in epidemiological studies documenting the dissemination of different strains of the disease.

The nucleotide sequences ISA1mta, ISA2cd, ISA3mx, ISA4ha and associated derivatives thereof when translated into protein sequences being composed of either identical or equivalent amino acids, should induce a response by the hosts immune system. This principle can be further expanded to use these proteins in diagnostics tests and vaccination procedures.

The invention claimed is:

1. An isolated polypeptide comprising an amino acid sequence as set forth in SEQ ID NO: 6, 7, or 8.

2. An immunogenic composition comprising the polypeptide of claim 1 and a pharmaceutically acceptable carrier.

3. A diagnostic composition comprising the polypeptide of claim 1.

4. A diagnostic kit comprising the polypeptide of claim 1.

5. The isolated polypeptide of claim 1, wherein the amino acid sequence is set forth in SEQ ID NO: 6.

6. The isolated polypeptide of claim 1, wherein the amino acid sequence is set forth in SEQ ID NO: 7.

7. The isolated polypeptide of claim 1, wherein the amino acid sequence is set forth in SEQ ID NO: 8.

8. An isolated polynucleotide comprising a nucleic acid sequence encoding the isolated polypeptide of claim 1.

9. The isolated polynucleotide of claim 8, wherein the nucleic acid sequence is set forth in SEQ ID NO:5.

* * * * *

SEQUENCE LISTING

<160> NUMBER OF SEQ ID NOS: 10

<210> SEQ ID NO 1
<211> LENGTH: 1821
<212> TYPE: DNA
<213> ORGANISM: Salmon Anaemia Virus

<400> SEQUENCE: 1

```
caagatggat aacctccgtg aatgcataaa ccgcaaaaga agactacttg ccttaccaga      60

tgttcctgaa acttcggatg cctttctaag tgatttgaga catctataca tgtgtgttgc     120

tttctgtgat caacacaaaa ccactggaga cgaatcaaga ttcaccaacc tggaattact     180

tgaccaagat gaagcactag gtgcccaaag agcttttgaa gccaaacatg gaataaaagg     240

aggttcttta ggagacgttc ttgaccatga actgaaaaag gtcattgaat ttacttttac     300

ttctggaagt ttgtatattg ccgaacaaag aaaaagaaag actcaagcag actcaataat     360

tgtgtgcgtt tcagaaggac ttaacgactt cagcgtatca cacggagtgc tagacatggg     420

acttgtggaa acaggggtga atgcagtaag agatttctgc acacaaaacg gaataccaat     480

gaagataaat caggtaggat ccacgagaac accaacaccg atcagcacat gcaaaatctc     540

tgaacaaata acacgacaga taaacagtac aattactgaa aggaaaatgg aaacagtact     600

ggcagcaatc gcaattaaac cagaactcaa actaactcag aaaggatgca gaccttgtaa     660

agaactagaa gatgaaaata ttctgtggat ggaccctcaa ttctgtgaaa ttgatgaaag     720

ttttccttac agaggagggc catacgggaa cttcctgcaa gaattgctgc ttacaaccaa     780

cgacgtagag accaacggga aagacagaga agaagtagta aagaagatac tggataacaa     840

ggcgttcacc gttgaaagtg gtgaatgcat aataacactt ccagacaaaa tgacttgttt     900

cggagaacag gagaagaaga gaccagcaac aatagacgaa gtgagaaccg caggagaaag     960

gtttgaacag agtgttaaac cgaaaaccca aagatatgga aggttatcag acaaatggat    1020

ggagcttgaa aagtttatct ttactgcaag caaaacagaa gtggatactt tcctttctgt    1080

agggaccgaa agacttgagt cggttggagt gtgtgtcgga gctttacaca gagcgaccac    1140

aaccaggata attagaccta tgattcaagg agggaaatgt tgggggatga tgttcaaaac    1200

aaagtccaaa atgggagaca cgaggaagga aggatactgt cacgcaatca ttttcggaaa    1260

aggggaagat aaatcaggac aaaacaagat gacaatgatg ggaaaaacag tacattggca    1320

tctaagagta gttaagtcta aaggagactg gatggcgcaa caactctgtg caaacaaaag    1380

cagaatatgg gaacatgacc ctgagctagt aacagaagga gtgacagttc taatgacgcc    1440

tttttctcag aaaattgcca ccattagtag atggagggca atgaggttag acagcatgtt    1500

tcatgtttct agtgcctggc atcattcacc tgcgtgtgaa gctgcatcgg caatgctgag    1560

aaagtttgtg gagatagtac atgccatcaa ccagaaaaga gattggggtg ttgtggggag    1620

tatggaggac atggtgaagg aagtggagga aataggggag cacttgcaga cggcatgtga    1680

ttttagagtt tacaacatgt gcaaagcctt gattcagaaa attgcagtca gtacccaatg    1740

agtggttatt tacttgtaaa ttgttgtgtg tttgacgata tgtatttgtc gacgcggccg    1800

cggtcgacgc ggccgcgaat t                                              1821
```

<210> SEQ ID NO 2
<211> LENGTH: 578
<212> TYPE: PRT
<213> ORGANISM: Salmon Anaemia Virus -continued

<400> SEQUENCE: 2

Met Asp Asn Leu Arg Glu Cys Ile Asn Arg Lys Arg Arg Leu Leu Ala
1               5                   10                  15

Leu Pro Asp Val Pro Glu Thr Ser Asp Ala Phe Leu Ser Asp Leu Arg
            20                  25                  30

His Leu Tyr Met Cys Val Ala Phe Cys Asp Gln His Lys Thr Thr Gly
        35                  40                  45

Asp Glu Ser Arg Phe Thr Asn Leu Glu Leu Leu Asp Gln Asp Glu Ala
    50                  55                  60

Leu Gly Ala Gln Arg Ala Phe Glu Ala Lys His Gly Ile Lys Gly Gly
65                  70                  75                  80

Ser Leu Gly Asp Val Leu Asp His Glu Leu Lys Lys Val Ile Glu Phe
                85                  90                  95

Thr Phe Thr Ser Gly Ser Leu Tyr Ile Ala Glu Gln Arg Lys Arg Lys
            100                 105                 110

Thr Gln Ala Asp Ser Ile Ile Val Cys Val Ser Glu Gly Leu Asn Asp
        115                 120                 125

Phe Ser Val Ser His Gly Val Leu Asp Met Gly Leu Val Glu Thr Gly
    130                 135                 140

Val Asn Ala Val Arg Asp Phe Cys Thr Gln Asn Gly Ile Pro Met Lys
145                 150                 155                 160

Ile Asn Gln Val Gly Ser Thr Arg Thr Pro Thr Pro Ile Ser Thr Cys
                165                 170                 175

Lys Ile Ser Glu Gln Ile Thr Arg Gln Ile Asn Ser Thr Ile Thr Glu
            180                 185                 190

Arg Lys Met Glu Thr Val Leu Ala Ala Ile Ala Ile Lys Pro Glu Leu
        195                 200                 205

Lys Leu Thr Gln Lys Gly Cys Arg Pro Cys Lys Glu Leu Glu Asp Glu
    210                 215                 220

Asn Ile Leu Trp Met Asp Pro Gln Phe Cys Glu Ile Asp Glu Ser Phe
225                 230                 235                 240

Pro Tyr Arg Gly Gly Pro Tyr Gly Asn Phe Leu Gln Glu Leu Leu Leu
                245                 250                 255

Thr Thr Asn Asp Val Glu Thr Asn Gly Lys Asp Arg Glu Glu Val Val
            260                 265                 270

Lys Lys Ile Leu Asp Asn Lys Ala Phe Thr Val Glu Ser Gly Glu Cys
        275                 280                 285

Ile Ile Thr Leu Pro Asp Lys Met Thr Cys Phe Gly Glu Gln Glu Lys
    290                 295                 300

Lys Arg Pro Ala Thr Ile Asp Glu Val Arg Thr Ala Gly Glu Arg Phe
305                 310                 315                 320

Glu Gln Ser Val Lys Pro Lys Thr Gln Arg Tyr Gly Arg Leu Ser Asp
                325                 330                 335

Lys Trp Met Glu Leu Glu Lys Phe Ile Phe Thr Ala Ser Lys Thr Glu
            340                 345                 350

Val Asp Thr Phe Leu Ser Val Gly Thr Glu Arg Leu Glu Ser Val Gly
        355                 360                 365

Val Cys Val Gly Ala Leu His Arg Ala Thr Thr Thr Arg Ile Ile Arg
    370                 375                 380

Pro Met Ile Gln Gly Gly Lys Cys Trp Gly Met Met Phe Lys Thr Lys
385                 390                 395                 400

Ser Lys Met Gly Asp Thr Arg Lys Glu Gly Tyr Cys His Ala Ile Ile
                405                 410                 415

-continued

```
Phe Gly Lys Gly Glu Asp Lys Ser Gly Gln Asn Lys Met Thr Met Met
            420                 425                 430

Gly Lys Thr Val His Trp His Leu Arg Val Val Lys Ser Lys Gly Asp
        435                 440                 445

Trp Met Ala Gln Gln Leu Cys Ala Asn Lys Ser Arg Ile Trp Glu His
    450                 455                 460

Asp Pro Glu Leu Val Thr Glu Gly Val Thr Val Leu Met Thr Pro Phe
465                 470                 475                 480

Ser Gln Lys Ile Ala Thr Ile Ser Arg Trp Arg Ala Met Arg Leu Asp
                485                 490                 495

Ser Met Phe His Val Ser Ser Ala Trp His His Ser Pro Ala Cys Glu
            500                 505                 510

Ala Ala Ser Ala Met Leu Arg Lys Phe Val Glu Ile Val His Ala Ile
        515                 520                 525

Asn Gln Lys Arg Asp Trp Gly Val Val Gly Ser Met Glu Asp Met Val
    530                 535                 540

Lys Glu Val Glu Glu Ile Gly Glu His Leu Gln Thr Ala Cys Asp Phe
545                 550                 555                 560

Arg Val Tyr Asn Met Cys Lys Ala Leu Ile Gln Lys Ile Ala Val Ser
                565                 570                 575

Thr Gln


<210> SEQ ID NO 3
<211> LENGTH: 2018
<212> TYPE: DNA
<213> ORGANISM: Salmon Anaemia Virus

<400> SEQUENCE: 3

gcaaagatyg ctcaaatccc aaaaataata cagaaaacgt ataagagatg gccgataaag     60

gtatgactta ttcttttgat gtcagagaca acaccttggt tgtaagaaga tctaccgcta    120

ctaaaagtgg cattaagatc tcctacagag aggatcgagg aacatcactt ctccaaaagg    180

cattcgccgg gacagaagat gaattctggg tggagttaga tcaagatgtc tacgttgaca    240

aaaagattag aaaattcctg gaagaagaga aaatgaagga catgagcaca agagtgtctg    300

gagcagtggc agcagcaatt gaaagatcag ttgaatttga caatttctca aaagaagcag    360

cagctaacat tgaaatggct ggtgtagatg atgaagaagc tggaggaagt ggtctggtag    420

acaacagaag gaagaacaaa ggggtctcaa acatggccta caatctgtct ctattcatag    480

ggatggtgtt tcctgctctc actactttct tcagtgctat cctatcagaa ggtgaaatga    540

gcatctggca aaatggacaa gcaatcatca gaattctggc actggcagat gaagacggaa    600

agagacaaac aagaacagga ggacagaggg tggacatggc tgatgtaacc aagctgaacg    660

tagtcacggc taacgggaaa gtcaagcaag ttgaagtaaa cttgaacgat ctcaaagcag    720

cattcaggca gagtagacct aaaagatcgg actacagaaa agggcaaggt tccaaggcta    780

cagaatcaag catctccaac caatgtatgg cactgattat gaaatctgtg ctgtcagcag    840

accaactttt tgctccggga gtgaagatga tgaggacgaa cggtttcaat gcgtcgtaca    900

caacactggc agaaggggca aacattccga gcaagtacct aagacacatg aggaactgcg    960

gaggagtagc tctggacctg atgggaatga agaggatcaa aaactcacct gaaggagcca   1020

agtctaagat cttttccatc atccagaaga aagtaagagg aagatgtcgc acagaggagc   1080

aacgcctcct gactagcgca ctgaaaatca gcgacggtga aaacaagttc cagagaatca   1140

tggacactct atgtacaagc ttcctgattg accctccaag aactaccaaa tgcttcattc   1200
```

-continued

```
cacctatttc cagtctcatg atgtacatcc aagaaggcaa ctctgtactg gcaatggatt   1260

tcatgaaaaa cggagaggac gcctgcaaga tctgcagaga agccaaactg aaagtggggg   1320

taaacagtac gttcacaatg tcagtagcta gaacatgcgt tgcagtgtca atggttgcaa   1380

cagctttttg ttctgcagat atcatcgaga atgcagtgcc tggttccgaa aggtacagat   1440

ccaacatcaa ggctaacaca accaaaccaa aaaaggactc cacttacaca attcaaggac   1500

ttagattgtc taacgtgagg tatgaagcaa gacctgaaac atcacaaagc aacacagaca   1560

gaagttggca agtgaacgtg actgacagct tcggaggact tgctgtgttc aaccaagggg   1620

caattagaga aatgctagga gacggaacat cagagacaac tagtgtgaac gtcagagccc   1680

tggtgaagag aattctgaaa tcagcttcag agaggagtgc aagagctgta aagacattta   1740

tggtgggaga acaagggaaa tcagctattg ttatctctgg tgtgggactg ttctctattg   1800

actttgaagg ggtagaggaa gcggaaagga taactgacat gacacctgaa attgagtttg   1860

acgaggacga cgaggaagag gaagacattg acatttagag tgacaattat gtaactttct   1920

aattacccta tattgtttga atatataatg aaactattgt gtgttaaagg ttgtgggttt   1980

gattattaaa tttaaattga aacggtattg acgatatt                           2018
```

```
<210> SEQ ID NO 4
<211> LENGTH: 616
<212> TYPE: PRT
<213> ORGANISM: Salmon Anaemia Virus

<400> SEQUENCE: 4

Met Ala Asp Lys Gly Met Thr Tyr Ser Phe Asp Val Arg Asp Asn Thr
1               5                   10                  15

Leu Val Val Arg Arg Ser Thr Ala Thr Lys Ser Gly Ile Lys Ile Ser
            20                  25                  30

Tyr Arg Glu Asp Arg Gly Thr Ser Leu Leu Gln Lys Ala Phe Ala Gly
        35                  40                  45

Thr Glu Asp Glu Phe Trp Val Glu Leu Asp Gln Asp Val Tyr Val Asp
    50                  55                  60

Lys Lys Ile Arg Lys Phe Leu Glu Glu Glu Lys Met Lys Asp Met Ser
65                  70                  75                  80

Thr Arg Val Ser Gly Ala Val Ala Ala Ala Ile Glu Arg Ser Val Glu
                85                  90                  95

Phe Asp Asn Phe Ser Lys Glu Ala Ala Ala Asn Ile Glu Met Ala Gly
            100                 105                 110

Val Asp Asp Glu Glu Ala Gly Gly Ser Gly Leu Val Asp Asn Arg Arg
        115                 120                 125

Lys Asn Lys Gly Val Ser Asn Met Ala Tyr Asn Leu Ser Leu Phe Ile
    130                 135                 140

Gly Met Val Phe Pro Ala Leu Thr Thr Phe Phe Ser Ala Ile Leu Ser
145                 150                 155                 160

Glu Gly Glu Met Ser Ile Trp Gln Asn Gly Gln Ala Ile Ile Arg Ile
                165                 170                 175

Leu Ala Leu Ala Asp Glu Asp Gly Lys Arg Gln Thr Arg Thr Gly Gly
            180                 185                 190

Gln Arg Val Asp Met Ala Asp Val Thr Lys Leu Asn Val Val Thr Ala
        195                 200                 205

Asn Gly Lys Val Lys Gln Val Glu Val Asn Leu Asn Asp Leu Lys Ala
    210                 215                 220

Ala Phe Arg Gln Ser Arg Pro Lys Arg Ser Asp Tyr Arg Lys Gly Gln
225                 230                 235                 240
```

-continued

```
Gly Ser Lys Ala Thr Glu Ser Ser Ile Ser Asn Gln Cys Met Ala Leu
                245                 250                 255

Ile Met Lys Ser Val Leu Ser Ala Asp Gln Leu Phe Ala Pro Gly Val
            260                 265                 270

Lys Met Met Arg Thr Asn Gly Phe Asn Ala Ser Tyr Thr Thr Leu Ala
        275                 280                 285

Glu Gly Ala Asn Ile Pro Ser Lys Tyr Leu Arg His Met Arg Asn Cys
    290                 295                 300

Gly Gly Val Ala Leu Asp Leu Met Gly Met Lys Arg Ile Lys Asn Ser
305                 310                 315                 320

Pro Glu Gly Ala Lys Ser Lys Ile Phe Ser Ile Ile Gln Lys Lys Val
                325                 330                 335

Arg Gly Arg Cys Arg Thr Glu Glu Gln Arg Leu Leu Thr Ser Ala Leu
            340                 345                 350

Lys Ile Ser Asp Gly Glu Asn Lys Phe Gln Arg Ile Met Asp Thr Leu
        355                 360                 365

Cys Thr Ser Phe Leu Ile Asp Pro Pro Arg Thr Thr Lys Cys Phe Ile
    370                 375                 380

Pro Pro Ile Ser Ser Leu Met Met Tyr Ile Gln Glu Gly Asn Ser Val
385                 390                 395                 400

Leu Ala Met Asp Phe Met Lys Asn Gly Glu Asp Ala Cys Lys Ile Cys
                405                 410                 415

Arg Glu Ala Lys Leu Lys Val Gly Val Asn Ser Thr Phe Thr Met Ser
            420                 425                 430

Val Ala Arg Thr Cys Val Ala Val Ser Met Val Ala Thr Ala Phe Cys
        435                 440                 445

Ser Ala Asp Ile Ile Glu Asn Ala Val Pro Gly Ser Glu Arg Tyr Arg
    450                 455                 460

Ser Asn Ile Lys Ala Asn Thr Thr Lys Pro Lys Lys Asp Ser Thr Tyr
465                 470                 475                 480

Thr Ile Gln Gly Leu Arg Leu Ser Asn Val Arg Tyr Glu Ala Arg Pro
                485                 490                 495

Glu Thr Ser Gln Ser Asn Thr Asp Arg Ser Trp Gln Val Asn Val Thr
            500                 505                 510

Asp Ser Phe Gly Gly Leu Ala Val Phe Asn Gln Gly Ala Ile Arg Glu
        515                 520                 525

Met Leu Gly Asp Gly Thr Ser Glu Thr Thr Ser Val Asn Val Arg Ala
    530                 535                 540

Leu Val Lys Arg Ile Leu Lys Ser Ala Ser Glu Arg Ser Ala Arg Ala
545                 550                 555                 560

Val Lys Thr Phe Met Val Gly Glu Gln Gly Lys Ser Ala Ile Val Ile
                565                 570                 575

Ser Gly Val Gly Leu Phe Ser Ile Asp Phe Glu Gly Val Glu Glu Ala
            580                 585                 590

Glu Arg Ile Thr Asp Met Thr Pro Glu Ile Glu Phe Asp Glu Asp Asp
        595                 600                 605

Glu Glu Glu Glu Asp Ile Asp Ile
    610                 615
```

<210> SEQ ID NO 5
<211> LENGTH: 1050
<212> TYPE: DNA
<213> ORGANISM: Salmon Anaemia Virus

```
<400> SEQUENCE: 5

atgtctggat ttaacctcga ggtaatggtg ccggaacaag gaggaaaagt ggtcttcagc     60

cttactgaaa cggggtcatg tgtctcgttt tacggagatg atgaaccagg tgaagggtcc    120

tgcgaacttg cctctgaaaa catggatttt ccaagttgtc ctctggggaa tggagatgac    180

ttctgtctgt cgctggcgct aagcacaatg agatggtctg ggatgaccaa gagaaacaac    240

ttcatggaca gattcattgg aagttttgtt cactgtacac cagtgatgat ctggtcgtat    300

ggaaatttgt ccaagaaaag ccatcacaaa atggtttgcc acacttgccc agacgagtac    360

aagttcagtg acaaggacga gatgcaggga tactatgagg gatgtctaga ggcttctact    420

gacattttcc ttgatgaact tgctactgtt gttacaggtg gcttctttcc tgtcggactc    480

aaaggttcct ggggaggatg gtacctcaag tacgtcaggt atgctggacc tcttgcggga    540

tcaagtggat tcattgtcaa tcaacgattc tacgacagag cccaaaacaa gactggatcc    600

agggttgtat ccatggttga aatggacgga gacggcttat cgttcatcta cgagaagcct    660

agcgtctacc atagtgatgg gtgcactggg tcagcagcga ggttctggaa acgggatcac    720

aatgagagag ctggagttga gcttagggct ggacttcact tcagaatgtg attggttgaa    780

aacttgttat gtaaacaaga attttgtgtt tttgtcagaa aaagaaattg ctgtaaacat    840

ggaagttgaa aaattcattt gtaatgagaa ctaaagatgt ctttgtgttc aaattttaac    900

taatgacaat atatgaaata tgtcgtacat ggtgttgatg ataattttta aaacgaaaag    960

gagaattttt actaaaataa aaaaaaaata aaaaaaaaaa aaaagaaaaa aaaaaaaaaa   1020

aaaaaaagtc gacatcgata cgcgtggtca                                    1050


<210> SEQ ID NO 6
<211> LENGTH: 256
<212> TYPE: PRT
<213> ORGANISM: Salmon Anaemia Virus

<400> SEQUENCE: 6

Met Ser Gly Phe Asn Leu Glu Val Met Val Pro Glu Gln Gly Gly Lys
1               5                   10                  15

Val Val Phe Ser Leu Thr Glu Thr Gly Ser Cys Val Ser Phe Tyr Gly
            20                  25                  30

Asp Asp Glu Pro Gly Glu Gly Ser Cys Glu Leu Ala Ser Glu Asn Met
        35                  40                  45

Asp Phe Pro Ser Cys Pro Leu Gly Asn Gly Asp Asp Phe Cys Leu Ser
    50                  55                  60

Leu Ala Leu Ser Thr Met Arg Trp Ser Gly Met Thr Lys Arg Asn Asn
65                  70                  75                  80

Phe Met Asp Arg Phe Ile Gly Ser Phe Val His Cys Thr Pro Val Met
                85                  90                  95

Ile Trp Ser Tyr Gly Asn Leu Ser Lys Lys Ser His His Lys Met Val
            100                 105                 110

Cys His Thr Cys Pro Asp Glu Tyr Lys Phe Ser Asp Lys Asp Glu Met
        115                 120                 125

Gln Gly Tyr Tyr Glu Gly Cys Leu Glu Ala Ser Thr Asp Ile Phe Leu
    130                 135                 140

Asp Glu Leu Ala Thr Val Val Thr Gly Gly Phe Phe Pro Val Gly Leu
145                 150                 155                 160

Lys Gly Ser Trp Gly Gly Trp Tyr Leu Lys Tyr Val Arg Tyr Ala Gly
                165                 170                 175
```

```
Pro Leu Ala Gly Ser Ser Gly Phe Ile Val Asn Gln Arg Phe Tyr Asp
            180                 185                 190

Arg Ala Gln Asn Lys Thr Gly Ser Arg Val Val Ser Met Val Glu Met
        195                 200                 205

Asp Gly Asp Gly Leu Ser Phe Ile Tyr Glu Lys Pro Ser Val Tyr His
    210                 215                 220

Ser Asp Gly Cys Thr Gly Ser Ala Ala Arg Phe Trp Lys Arg Asp His
225                 230                 235                 240

Asn Glu Arg Ala Gly Val Glu Leu Arg Ala Gly Leu His Phe Arg Met
                245                 250                 255


<210> SEQ ID NO 7
<211> LENGTH: 140
<212> TYPE: PRT
<213> ORGANISM: Salmon Anaemia Virus

<400> SEQUENCE: 7

Met Ser Gly Phe Asn Leu Glu Val Met Val Pro Glu Gln Gly Gly Lys
1               5                   10                  15

Val Val Phe Ser Leu Thr Glu Thr Gly Ser Cys Val Ser Phe Tyr Gly
            20                  25                  30

Asp Asp Glu Pro Gly Gly Phe Phe Pro Val Gly Leu Lys Gly Ser Trp
        35                  40                  45

Gly Gly Ser Tyr Leu Lys Tyr Val Arg Tyr Ala Gly Pro Leu Ala Gly
    50                  55                  60

Ser Ser Gly Phe Ile Val Asn Gln Arg Phe Tyr Asp Arg Ala Gln Asn
65                  70                  75                  80

Lys Thr Gly Ser Arg Val Val Ser Met Val Glu Met Asp Gly Asp Gly
                85                  90                  95

Leu Ser Phe Ile Tyr Glu Lys Pro Ser Val Tyr His Ser Asp Gly Cys
            100                 105                 110

Thr Gly Ser Ala Ala Arg Phe Trp Lys Arg Asp His Asn Glu Arg Ala
        115                 120                 125

Gly Val Glu Leu Arg Ala Gly Leu His Phe Arg Met
    130                 135                 140


<210> SEQ ID NO 8
<211> LENGTH: 146
<212> TYPE: PRT
<213> ORGANISM: Salmon Anaemia Virus

<400> SEQUENCE: 8

Met Asn Leu Leu Leu Leu Leu Gln Val Ala Ser Phe Leu Ser Asp Ser
1               5                   10                  15

Lys Val Pro Gly Glu Asp Gly Thr Ser Ser Thr Ser Gly Met Leu Asp
            20                  25                  30

Leu Leu Arg Asp Gln Val Asp Ser Leu Ser Ile Asn Asp Ser Thr Thr
        35                  40                  45

Glu Pro Lys Thr Arg Leu Asp Pro Gly Leu Tyr Pro Trp Leu Lys Trp
    50                  55                  60

Thr Glu Thr Ala Tyr Arg Ser Ser Thr Arg Ser Leu Ala Ser Thr Ile
65                  70                  75                  80

Val Met Gly Ala Leu Gly Gln Gln Arg Gly Ser Gly Asn Gly Ile Thr
                85                  90                  95

Met Arg Glu Leu Glu Leu Ser Leu Gly Leu Asp Phe Thr Ser Glu Cys
            100                 105                 110
```

-continued

Asp Trp Leu Lys Thr Cys Tyr Val Asn Lys Asn Phe Val Phe Leu Ser
115 120 125

Glu Lys Glu Ile Ala Val Asn Met Glu Val Glu Lys Phe Ile Cys Asn
130 135 140

Glu Asn
145

<210> SEQ ID NO 9
<211> LENGTH: 1033
<212> TYPE: DNA
<213> ORGANISM: Salmon Anaemia Virus

<400> SEQUENCE: 9
cagtcgtcta tgtcttagaa accatcctga caccacctgg ataggtgact cccgaagcga 60
tcaatcaagg gtgaaccaac agtctcttga tctggttaca aacttcaagg gaattctaca 120
agccaagaac gggaatggtc tcatgaagca gatgagcgga aggttcccaa gtgattggta 180
ccaacctact acaaagtata ggattctata cattggtaca aacgactgca ctgagggccc 240
taacgacgtg atcataccga cgtcaatgac actagacaat gtggcaaggg acctgtacct 300
gggagcatgt cgaggagatg taagagtgac accaaccttc gtgggagcag ctgagcttgg 360
actgattggg agaacagatg ccttaacagg attttctgta aaggtgctga ctttcaacaa 420
ccctactatt gtagtagttg gactaaatgg aatgtcagga atctacaagg tctgcattgc 480
tgcctcttct ggaaacgtag gcggagtcaa cttggtgaac ggatgcggat acttcagcgc 540
tcctctgaga ttcgacaact tcaaaggaca gatctacgtg tcagacacct ttgaagtcag 600
aggaacaaag aacaaatgtg tcatacttag atcttctagc aatgctcctt tgtgtacaca 660
tatcaaaaga aacattgagt tggatgagta cgttgacaca ccaaacactg gggcgtata 720 tccttctgat gggtttgatt ctcttcacgg ctctgcttcg attagaactt ttttaacaga 780
ggcactgaca tgtccaggtg tagattggga cagaattgat gcagcttcat gcgagtatga 840
cagttgtcct aaacttgtga aagaatttga ccaaacaggg ctcggaaaca cagatactca 900
aataatgaga gagctagaag cacaaaagga gatgattggt aaacttggca gaaacattac 960
agacgtaaac aacagagtag atgctattcc accacagctt agcaacatct tcatctctat 1020
gggagtggca ggt 1033

<210> SEQ ID NO 10
<211> LENGTH: 344
<212> TYPE: PRT
<213> ORGANISM: Salmon Anaemia Virus

<400> SEQUENCE: 10

Ser Arg Leu Cys Leu Arg Asn His Pro Asp Thr Thr Trp Ile Gly Asp
1 5 10 15

Ser Arg Ser Asp Gln Ser Arg Val Asn Gln Gln Ser Leu Asp Leu Val
20 25 30

Thr Asn Phe Lys Gly Ile Leu Gln Ala Lys Asn Gly Asn Gly Leu Met
35 40 45

Lys Gln Met Ser Gly Arg Phe Pro Ser Asp Trp Tyr Gln Pro Thr Thr
50 55 60

Lys Tyr Arg Ile Leu Tyr Ile Gly Thr Asn Asp Cys Thr Glu Gly Pro
65 70 75 80

Asn Asp Val Ile Ile Pro Thr Ser Met Thr Leu Asp Asn Val Ala Arg
85 90 95

-continued

```
Asp Leu Tyr Leu Gly Ala Cys Arg Gly Asp Val Arg Val Thr Pro Thr
            100                 105                 110

Phe Val Gly Ala Ala Glu Leu Gly Leu Ile Gly Arg Thr Asp Ala Leu
        115                 120                 125

Thr Gly Phe Ser Val Lys Val Leu Thr Phe Asn Asn Pro Thr Ile Val
    130                 135                 140

Val Val Gly Leu Asn Gly Met Ser Gly Ile Tyr Lys Val Cys Ile Ala
145                 150                 155                 160

Ala Ser Ser Gly Asn Val Gly Gly Val Asn Leu Val Asn Gly Cys Gly
                165                 170                 175

Tyr Phe Ser Ala Pro Leu Arg Phe Asp Asn Phe Lys Gly Gln Ile Tyr
            180                 185                 190

Val Ser Asp Thr Phe Glu Val Arg Gly Thr Lys Asn Lys Cys Val Ile
        195                 200                 205

Leu Arg Ser Ser Ser Asn Ala Pro Leu Cys Thr His Ile Lys Arg Asn
    210                 215                 220

Ile Glu Leu Asp Glu Tyr Val Asp Thr Pro Asn Thr Gly Gly Val Tyr
225                 230                 235                 240

Pro Ser Asp Gly Phe Asp Ser Leu His Gly Ser Ala Ser Ile Arg Thr
                245                 250                 255

Phe Leu Thr Glu Ala Leu Thr Cys Pro Gly Val Asp Trp Asp Arg Ile
            260                 265                 270

Asp Ala Ala Ser Cys Glu Tyr Asp Ser Cys Pro Lys Leu Val Lys Glu
        275                 280                 285

Phe Asp Gln Thr Gly Leu Gly Asn Thr Asp Thr Gln Ile Met Arg Glu
    290                 295                 300

Leu Glu Ala Gln Lys Glu Met Ile Gly Lys Leu Gly Arg Asn Ile Thr
305                 310                 315                 320

Asp Val Asn Asn Arg Val Asp Ala Ile Pro Pro Gln Leu Ser Asn Ile
                325                 330                 335

Phe Ile Ser Met Gly Val Ala Gly
            340
```